(12) United States Patent
Lange et al.

(10) Patent No.: US 11,053,233 B2
(45) Date of Patent: Jul. 6, 2021

(54) SOLID FORM OF (S)-[2-CHLORO-4-FLUORO-5-(7-MORPHOLIN-4-YL-QUINAZOLIN-4-YL)PHENYL]-(6-METHOXY-PYRIDAZIN-3-YL)-METHANOL

(71) Applicant: Merck Patent GmbH, Darmstadt (DE)

(72) Inventors: Michael Lange, Darmstadt (DE); Clemens Kuehn, Darmstadt (DE); Thomas Fuchss, Bensheim-Auerbach (DE); David Maillard, Darmstadt (DE); Marcel Breuning, Frankfurt am Main (DE); Marco Poma, Rome (IT); Edoardo Burini, Guidonia Montecelio (IT)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/498,905

(22) PCT Filed: Mar. 28, 2018

(86) PCT No.: PCT/EP2018/057875
§ 371 (c)(1),
(2) Date: Sep. 27, 2019

(87) PCT Pub. No.: WO2018/178133
PCT Pub. Date: Oct. 14, 2018

(65) Prior Publication Data
US 2020/0123144 A1    Apr. 23, 2020

(30) Foreign Application Priority Data
Mar. 30, 2017   (EP) .................................. 17163826

(51) Int. Cl.
*C07D 413/14* (2006.01)
*B01D 9/00* (2006.01)

(52) U.S. Cl.
CPC ......... *C07D 413/14* (2013.01); *B01D 9/0054* (2013.01); *C07B 2200/13* (2013.01)

(58) Field of Classification Search
CPC .................................................... C07D 413/14
See application file for complete search history.

(56) References Cited

U.S. PATENT DOCUMENTS

| 9,732,094 B2 | 8/2017 | Fuchss et al. |
| 10,172,859 B2 | 1/2019 | Fuchss et al. |
| 10,383,874 B2 | 8/2019 | Fuchss et al. |
| 2016/0083401 A1 | 3/2016 | Fuchss et al. |
| 2017/0290836 A1 | 10/2017 | Fuchss et al. |
| 2019/0142833 A1 | 5/2019 | Fuchss et al. |

FOREIGN PATENT DOCUMENTS

WO   2014/183850   11/2014

OTHER PUBLICATIONS

Cancer and Metastasis Reviews (1998), 17(1), 91-106.*
Science (1999), vol. 286, 531-537.*
International Search Report dated May 17, 2018 in PCT/EP2018/057875.
Written Opinion dated May 17, 2018 in PCT/EP2018/057875.
Byrn et al., "Pharmaceutical Solids: A Strategic Approach to Regulatory Considerations," Pharmaceutical Research, vol. 12, No. 7, 1995, pp. 945-954 XP055395840.
Mino R. Caira, "Crystalline Polymorphism of Organic Compounds," Department of Chemistry, University of Cape Town, Rondebosch 7700, South Africa, Topics in Current Chemistry, vol. 198, Jan. 1998, pp. 163-208 XP8166276A.
Smith et al., "*The DNA-dependent protein kinase*," Genes & Development 13:916-934. 1999.

* cited by examiner

*Primary Examiner* — Rebecca L Anderson
(74) *Attorney, Agent, or Firm* — Grüneberg and Myers PLLC

(57) ABSTRACT

An anhydrous disordered crystalline (S)-[2-chloro-4-fluoro-5-(7-morpholin-4-yl-quinazolin-4-yl)-phenyl]-(6-methoxy-pyridazin-3-yl)-methanol can be used in pharmaceutical compositions.

16 Claims, 3 Drawing Sheets

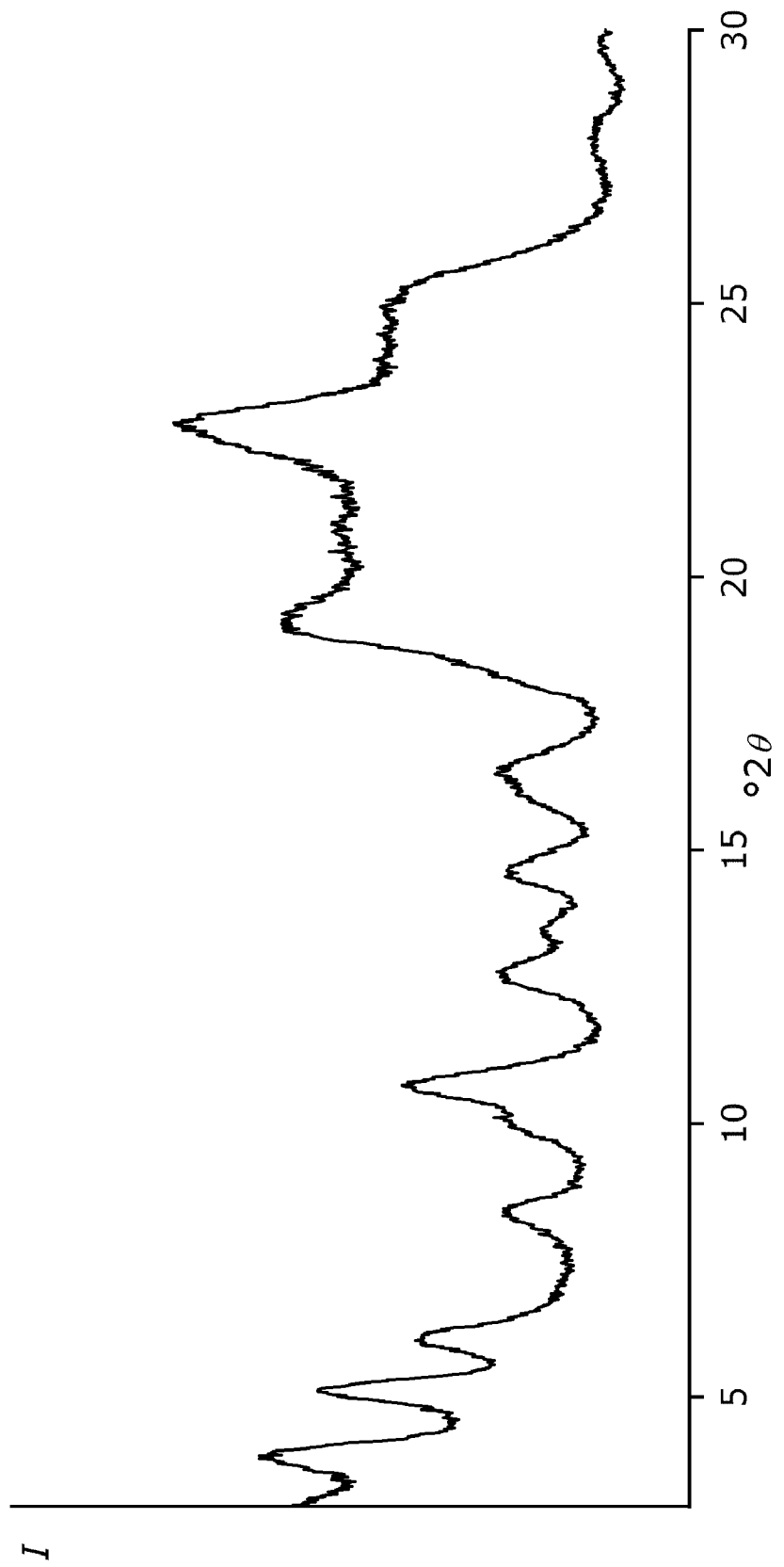
Figure 1: Powder X-ray diffractogram

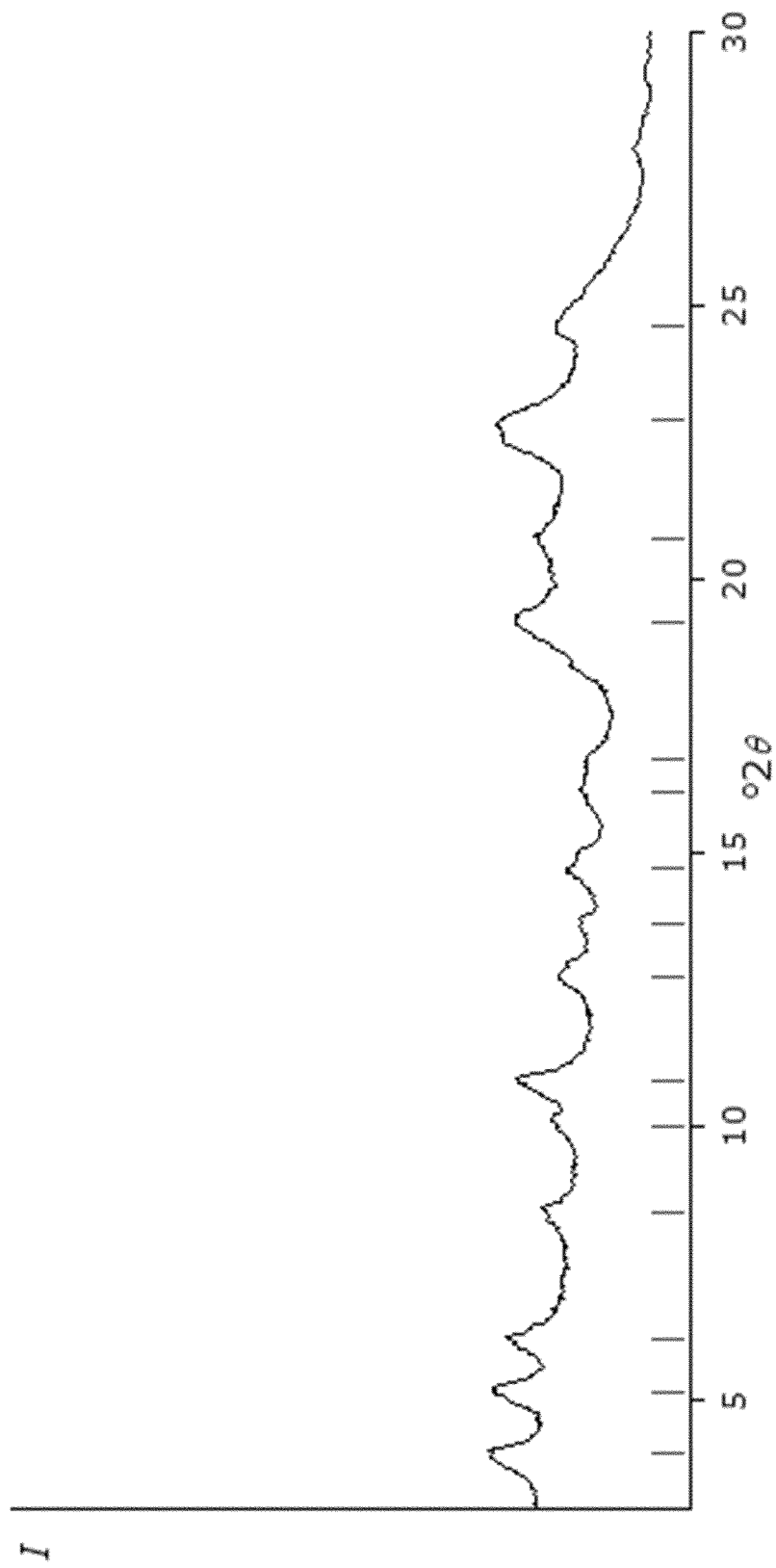
Figure 2: Further powder X-ray diffractogram

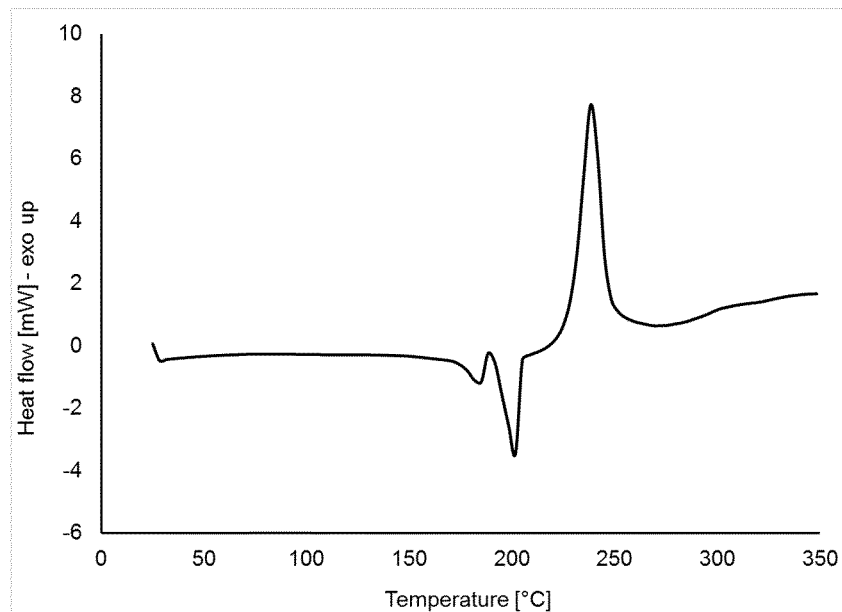
Figure 3: DSC scan
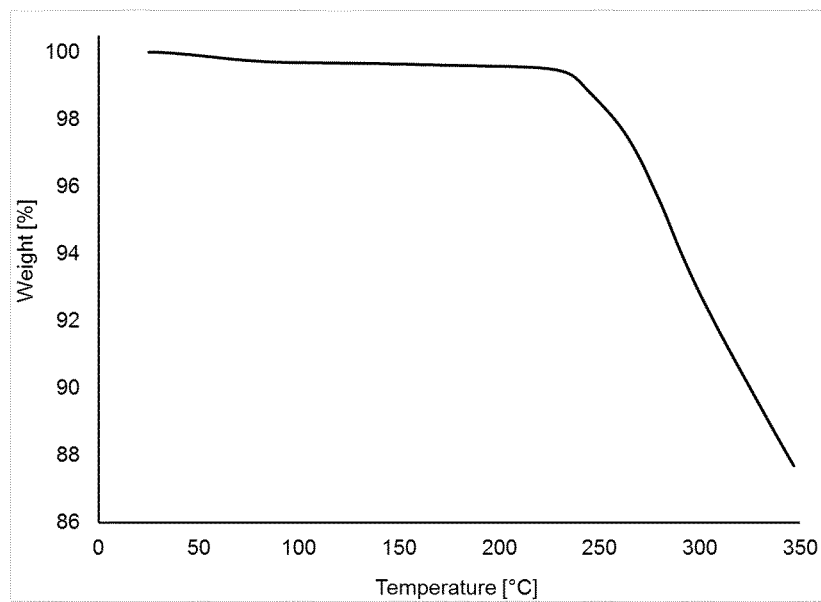
Figure 4: TGA profile

SOLID FORM OF (S)-[2-CHLORO-4-FLUORO-5-(7-MORPHOLIN-4-YL-QUINAZOLIN-4-YL) PHENYL]-(6-METHOXY-PYRIDAZIN-3-YL)-METHANOL

CROSS-REFERENCE TO RELATED APPLICATIONS

This application is a National Stage entry under § 371 of International Application No. PCT/EP2018/057875, filed on Mar. 28, 2018, and which claims the benefit of European Application No. 17163826.5, filed on Mar. 30, 2017.

BACKGROUND OF THE INVENTION

The present invention relates to anhydrous disordered crystalline (S)-[2-chloro-4-fluoro-5-(7-morpholin-4-yl-quinazolin-4-yl)phenyl]-(6-methoxy-pyridazin-3-yl)-methanol, as well as a method of making same, and pharmaceutical compositions and medical uses thereof.

(S)-[2-chloro-4-fluoro-5-(7-morpholin-4-yl-quinazolin-4-yl)phenyl]-(6-methoxy-pyridazin-3-yl)-methanol, the compound depicted below, is disclosed as Example 136 in WO 2014/183850, as one member of a family of arylquinazolines which have been found to have valuable pharmacological properties.

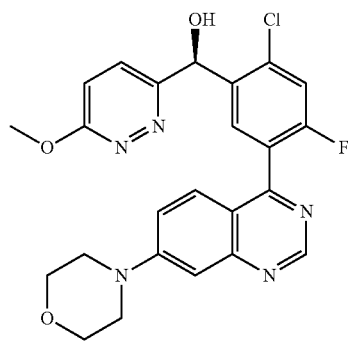 [SMILES: COc1ccc([C@@H](O)c2cc(-c3ncnc4cc(N5CCOCC5)ccc34)c(F)cc2Cl)nn1]

(S)-[2-chloro-4-fluoro-5-(7-morpholin-4-yl-quinazolin-4-yl)phenyl]-(6-methoxy-pyridazin-3-yl)-methanol is a potent and selective inhibitor of DNA-dependent protein kinase (DNA-PK) activity translating into potent inhibition of DNA-PK autophosphorylation in cancer cell lines, which has been demonstrated both by in vitro as well as in vivo data. It can therefore be used, in particular, for the sensitisation of cancer cells to anticancer agents and/or ionising radiation.

Human genetic material in the form of DNA is constantly subjected to attack by reactive oxygen species (ROSs), which are formed principally as by-products of oxidative metabolism. ROSs are capable of causing DNA damage in the form of single-strand breaks. Double-strand breaks can arise if prior single-strand breaks occur in close proximity. In addition, single- and double-strand breaks may be caused if the DNA replication fork encounters damaged base patterns. Furthermore, exogenous influences, such as ionising radiation (for example gamma or particle radiation), and certain anticancer medicaments (for example bleomycin) are capable of causing DNA double-strand breaks. DSBs may furthermore occur as intermediates of somatic recombination, a process which is important for the formation of a functional immune system of all vertebrates.

If DNA double-strand breaks are not repaired or are repaired incorrectly, mutations and/or chromosome aberrations may occur, which may consequently result in cell death. In order to counter the severe dangers resulting from DNA double-strand breaks, eukaryotic cells have developed a number of mechanisms to repair them. Higher eukaryotes use predominantly so-called non-homologous end-joining, in which the DNA-dependent protein kinase (DNA-PK) adopts the key role. DNA-dependent protein kinase (DNA-PK) is a serine/threonine protein kinase which is activated in conjunction with DNA. Biochemical investigations have shown that DNA-PK is activated most effectively by the occurrence of DNA-DSBs. Cell lines whose DNA-PK components have mutated and are non-functional have proven to be radiation-sensitive (Smith and Jackson, 1999). DSBs are considered the most lethal type of DNA damage if left unrepaired.

WO 2014/183850 discloses that the preparation of compound 136 (S)-[2-Chloro-4-fluoro-5-(7-morpholin-4-yl-quinazolin-4-yl)phenyl]-(6-methoxy-pyridazin-3-yl)-methanol free base was carried out in analogy to previous examples and indicates that chiral separation was carried out by SFC (Supercritical Fluid Chromatography), using a certain chiral setup. However, no solid form of the enantiomer is disclosed.

It was an object of the present invention to develop a solid form of (S)-[2-Chloro-4-fluoro-5-(7-morpholin-4-yl-quinazolin-4-yl)phenyl]-(6-methoxy-pyridazin-3-yl)-methanol that would be suitable for use in a pharmaceutical formulation.

SUMMARY OF THE INVENTION

The present invention is directed to anhydrous disordered crystalline (S)-[2-chloro-4-fluoro-5-(7-morpholin-4-yl-quinazolin-4-yl)phenyl]-(6-methoxy-pyridazin-3-yl)-methanol.

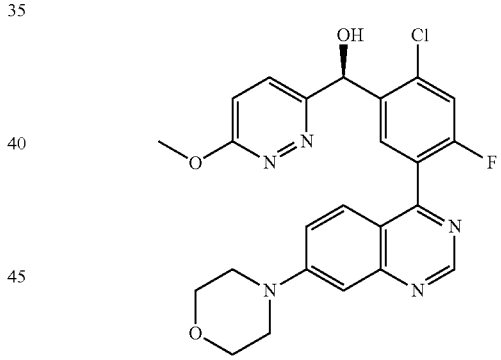

The present invention further pertains to a method of preparing anhydrous disordered crystalline (S)-[2-chloro-4-fluoro-5-(7-morpholin-4-yl-quinazolin-4-yl)phenyl]-(6-methoxy-pyridazin-3-yl)-methanol, a pharmaceutical composition comprising same, and its use in the treatment of cancer, either alone or in combination with radiotherapy and/or chemotherapy.

BRIEF DESCRIPTION OF THE FIGURES

FIG. 1 shows a powder X-ray diffractogram (PXRD) of anhydrous disordered crystalline (S)-[2-chloro-4-fluoro-5-(7-morpholin-4-yl-quinazolin-4-yl)phenyl]-(6-methoxy-pyridazin-3-yl)-methanol.

FIG. 2 shows a further powder X-ray diffractogram (PXRD) of anhydrous disordered crystalline (S)-[2-chloro-4-fluoro-5-(7-morpholin-4-yl-quinazolin-4-yl)phenyl]-(6-methoxy-pyridazin-3-yl)-methanol.

FIG. 3 shows a DSC scan of anhydrous disordered crystalline (S)-[2-chloro-4-fluoro-5-(7-morpholin-4-yl-quinazolin-4-yl)phenyl]-(6-methoxy-pyridazin-3-yl)-methanol.

FIG. 4 shows a TGA profile of anhydrous disordered crystalline (S)-[2-chloro-4-fluoro-5-(7-morpholin-4-yl-quinazolin-4-yl)phenyl]-(6-methoxy-pyridazin-3-yl)-methanol.

DETAILED DESCRIPTION OF THE INVENTION

As explained above, the synthesis of (S)-[2-chloro-4-fluoro-5-(7-morpholin-4-yl-quinazolin-4-yl)phenyl]-(6-methoxy-pyridazin-3-yl)-methanol as such is described in WO 2014/183850, the entirety of which is disclosed by reference herein. A solid state form of the enantiomer is not disclosed in the application.

The present invention provides anhydrous disordered crystalline (S)-[2-chloro-4-fluoro-5-(7-morpholin-4-yl-quinazolin-4-yl)phenyl]-(6-methoxy-pyridazin-3-yl)-methanol, which has very favourable properties.

Any reference herein to (S)-[2-chloro-4-fluoro-5-(7-morpholin-4-yl-quinazolin-4-yl)phenyl]-(6-methoxy-pyridazin-3-yl)-methanol refers to the free form of the molecule as depicted above, rather than a salt form.

An powder X-ray diffraction pattern of said anhydrous disordered crystalline (S)-[2-chloro-4-fluoro-5-(7-morpholin-4-yl-quinazolin-4-yl)phenyl]-(6-methoxy-pyridazin-3-yl)-methanol is depicted in FIG. 1. As apparent from FIG. 1, the peaks of the PXRD pattern are significantly broadened as compared to a regular ordered crystalline form. This is hypothesized as being due to the absence of a strict long-range crystalline periodicity.

Accordingly, the anhydrous disordered crystalline (S)-[2-chloro-4-fluoro-5-(7-morpholin-4-yl-quinazolin-4-yl)phenyl]-(6-methoxy-pyridazin-3-yl)-methanol can be characterized as having a powder X-ray diffraction pattern substantially in accordance with FIG. 1.

As a result of the disorder in the crystal structure, peak locations and shapes vary more than in case of ordered crystalline forms. This is illustrated by the PXRD illustrated in FIG. 2.

As apparent from FIGS. 1 and 2, broadened peaks occur at one ore more of:

TABLE 1

List of X-ray peaks of anhydrous disordered crystalline form

| Peak No. | Measurement 1 °2θ (Cu-Kα₁ radiation) ± 0.3° (preferably ± 0.2°) | Measurement 2 °2θ (Cu-Kα₁ radiation) ± 0.3° (preferably ± 0.2°) |
| --- | --- | --- |
| 1 | 3.1 | |
| 2 | 3.9 | 4.0 |
| 3 | 5.1 | 5.1 |
| 4 | 6.1 | 6.1 |
| 5 | 8.4 | 8.4 |
| 6 | 9.9 | 10.0 |
| 7 | 10.7 | 10.8 |
| 8 | 12.7 | 12.7 |
| 9 | 13.5 | 13.7 |
| 10 | 14.6 | 14.7 |
| 11 | 16.0 | 16.1 |
| 12 | 16.5 | 16.7 |
| 13 | 18.0 | |
| 14 | 19.0 | 19.2 |
| 15 | 20.9 | 20.7 |
| 16 | 21.9 | |
| 17 | 22.8 | 22.9 |
| 18 | 24.0 | |
| 19 | 24.9 | 24.6 |
| 20 | 25.4 | |

In other words, the present invention provides anhydrous disordered crystalline (S)-[2-chloro-4-fluoro-5-(7-morpholin-4-yl-quinazolin-4-yl)phenyl]-(6-methoxy-pyridazin-3-yl)-methanol, which is characterized by an Powder X-ray diffraction pattern having at least two peaks at degrees two theta selected from 3.9, 5.1, 6.1, 8.4, 10.7, 12.7, 14.6, and 22.8, each ±0.3 degrees two theta (preferably each ±0.2 degrees two theta), wherein each of the at least two peaks is characterized by having a full width at half maximum (FWHM) of equal to or greater than 0.2 degrees two theta. The powder X-ray diffraction pattern may also have three, four, five or six peaks at degrees two theta selected from 3.9, 5.1, 6.1, 8.4, 10.7, 12.7, 14.6, and 22.8, each ±0.3 degrees two theta (preferably each ±0.2 degrees two theta). The anhydrous disordered crystalline form may further be characterized in that the powder X-ray diffraction pattern has at least one further peak, for instance two, three, four, five or more further peaks at degrees two theta selected from 3.1, 9.9, 13.5, 16.0, 16.5, 18.0, 19.0, 20.9, 21.9, 22.8, 24.0, 24.9, and 25.4 each ±0.3, preferably ±0.2 degrees two theta.

The powder X-ray diffraction pattern referred to above was recorded using Cu—K$_{α1}$ radiation (λ=1.54 Å). Generally, powder X-ray diffraction patterns can be obtained by standard techniques known in the art, such as described in the European Pharmacopeia 6$^{th}$ Edition chapter 2.9.33. Further details regarding the powder X-ray diffraction method that has been employed in the recording of the powder X-ray diffraction pattern peaks forming the basis for the above values will be described further below.

The term "peak" is used herein in accordance with its established meaning in the art and synonymously with the term "maximum". As will be understood by the person skilled in the art, relative intensities (intensity I) in such diffraction patterns may vary to a relatively large extent, for instance up to 20 percent. A diffraction pattern would be "substantially in accordance" with that in FIG. 1 or 2, if a peak is within an experimental error of about ±0.3, preferably ±0.2°2θ at the indicated diffraction angle.

The anhydrous disordered crystalline form is a strongly disordered variety of crystalline Form I, which is described in a co-pending patent application and which crystallises in the orthorhombic space group P2₁2₁2₁ with the lattice parameters a=4.8 Å, b=27.5 Å, c=33.3 and α=β=γ=90°. Said crystalline Form I may be further characterized in that there are 8 formula units per unit cell and the unit cell volume is 4436 Å³, and the calculated density is 1.44 g/cm³. These data were generated based upon single crystal X-ray structure data using a Rigaku SuperNova diffractometer, equipped with CCD detector using Cu-Kα radiation at 200 K.

Thus, the XRPD diffractogram results from peak broadening of the peaks characterizing the spectrum of the ordered crystalline form, beyond a full width at half maximum (FWHM) of equal to or greater than 0.2 degrees two theta, which diffractogram has sharp peaks at 4.1, 5.2, 6.1, 8.3, 8.5, 10.1, 10.9, 12.7, 13.0, 13.8, 14.7, 15.0, 18.6, 19.2, 20.0, 20.5, 20.8, 21.3, 22.0, 22.4, 22.8, 23.4, 24.4, each ±0.2°2θ: Peaks which would appear particularly suited to distinguish said crystalline form from other crystalline forms may be seen in one or more of the peaks at 4.1, 5.2, 8.3, 8.5, 10.1, 10.9, 12.7, 13.0 and 21.3°2θ, each ±0.2°2θ.

In terms of thermal behaviour, besides small weight loss of <0.5% m/m up to 100° C., the anhydrous disordered crystalline form according to the present invention shows no thermal events prior to melting/decomposition above 150° C., as apparent from the DSC scan and TGA profile as depicted in FIGS. 3 and 4. The anhydrous disordered crystalline form exhibits high chemical and physical stability upon long-term DS (drug substance) stability investigations up to 40° C./75% relative humidity.

The anhydrous disordered crystalline (S)-[2-chloro-4-fluoro-5-(7-morpholin-4-yl-quinazolin-4-yl)phenyl]-(6-methoxy-pyridazin-3-yl)-methanol according to the present invention, also has solubility characteristics that render it suitable for biorelevant intestinal media. It can be characterized by one or more of the following:

| Medium | pH of medium | Solubility [µg/mL] | T [° C.] |
| --- | --- | --- | --- |
| SGF | 1.2 | 2024 ± 67 | 37 |
| FaSSIF | 6.5 | 10 ± 1 | 37 |
| FeSSIF | 5.0 | 56 ± 2 | 37 |

Solubility measurements were carried out in accordance with the method described further below.

It is noted that the solubility of the anhydrous disordered form is significantly better than that of the anhydrous ordered crystalline compound mentioned before. For instance, at pH 1.2, it has more than double the solubility of the crystalline form.

A further advantage of the anhydrous disordered form according to the present invention is that it has good and consistent manufacturability in large scale. This distinguishes the form according to the present invention from the amorphous state, for instance, which would be available through lyophilisation of the enantiomer obtained as described in WO 2014/183850 from acetonitrile and water.

The present invention further pertains to a process for preparing anhydrous disordered crystalline (S)-[2-chloro-4-fluoro-5-(7-morpholin-4-yl-quinazolin-4-yl)phenyl]-(6-methoxy-pyridazin-3-yl)-methanol, comprising antisolvent precipitation of (S)-[2-chloro-4-fluoro-5-(7-morpholin-4-yl-quinazolin-4-yl)phenyl]-(6-methoxy-pyridazin-3-yl)-methanol.

Preferably, the process for preparing said anhydrous disordered crystalline form comprises
a) preparing a clear solution of (S)-[2-chloro-4-fluoro-5-(7-morpholin-4-yl-quinazolin-4-yl)phenyl]-(6-methoxy-pyridazin-3-yl)-methanol in a solvent or solvent mixture, optionally with heating,
b) combining the clear solution with an anti-solvent such as to generate a suspension of (S)-[2-chloro-4-fluoro-5-(7-morpholin-4-yl-quinazolin-4-yl)phenyl]-(6-methoxy-pyridazin-3-yl)-methanol in solvent/antisolvent mixture,
c) separating the obtained anhydrous disordered crystalline (S)-[2-chloro-4-fluoro-5-(7-morpholin-4-yl-quinazolin-4-yl)phenyl]-(6-methoxy-pyridazin-3-yl)-methanol from the solvent/antisolvent mixture, and
d) drying the anhydrous disordered crystalline (S)-[2-chloro-4-fluoro-5-(7-morpholin-4-yl-quinazolin-4-yl)phenyl]-(6-methoxy-pyridazin-3-yl)-methanol.

Suitable solvents or solvent mixtures include, for instance, DMSO (dimethylsulfoxide), dichloromethane, methanol, 1,4-dioxane, tetrahydrofurane, and mixtures of two or more thereof, such as dichloromethane/methanol, to name but a few examples.

Suitable antisolvents include, for instance, acetone, n-heptane and water.

Any reference to water is to be understood as referring to deionised distilled water.

Suitable solvent/antisolvent systems for use in the process according to the present invention include: dichloromethane and n-heptane; methanol and water; 1,4-dioxane and water; tetrahydrofurane and n-heptane.

Preparation of the clear solution may include filtering the solvent or solvent mixture containing the (S)-[2-chloro-4-fluoro-5-(7-morpholin-4-yl-quinazolin-4-yl)phenyl]-(6-methoxy-pyridazin-3-yl)-methanol. It may, in the alternative or in addition, comprise concentrating the solution, for instance by way of evaporation.

The separating step c) may be effected by filtration or centrifugation, for instance.

Drying of the crystalline compound according to step d) of the process may be under vacuum, or reduced pressure, for instance, or under inert gas, such as nitrogen, in particular dry nitrogen. Furthermore, drying may be at room temperature or at elevated temperature, for instance at at least 40° C. or more, for instance 50° C. or more, for instance 60° C. or more, or 70° C. or more. The drying conditions are chosen in dependence of the solvent/solvent mixture used in the preparation of the crystalline material, as will be further exemplified with reference to the exemplary embodiments described in detail below.

Accordingly, the present invention further pertains to anhydrous disordered crystalline (S)-[2-chloro-4-fluoro-5-(7-morpholin-4-yl-quinazolin-4-yl)phenyl]-(6-methoxy-pyridazin-3-yl)-methanol, which is obtainable by antisolvent preparation, in particular using a solvent/antisolvent system as mentioned above.

In a further aspect, the present invention provides a pharmaceutical formulation comprising said anhydrous disordered crystalline (S)-[2-chloro-4-fluoro-5-(7-morpholin-4-yl-quinazolin-4-yl)phenyl]-(6-methoxy-pyridazin-3-yl)-methanol, optionally and preferably in combination with one or more pharmaceutically acceptable excipients.

Preferably, the pharmaceutical dosage form is for oral administration. Pharmaceutical dosage forms may comprise any dosage form wherein the material is contained in its anhydrous disordered crystalline form, including in particular solid dosage forms, such as capsules, tablets, lozenges, pills, powders, granules or ointments or sprays. Typically, the pharmaceutical dosage form comprises one or more excipients.

In one aspect, the pharmaceutical dosage form is a tablet and comprises the anhydrous disordered crystalline compound, as well as one or more excipients selected, for instance, from: a) a filler, b) a binder, c) a humectant, d) a disintegrating agent, e) a wicking agent, f) a matrix former, and g) a lubricant.

The present invention further pertains to the use of anhydrous disordered crystalline (S)-[2-chloro-4-fluoro-5-(7-morpholin-4-yl-quinazolin-4-yl)phenyl]-(6-methoxy-pyridazin-3-yl)-methanol, or a pharmaceutical dosage form comprising same, for use in the treatment of cancer.

In some embodiments, the cancer treatment further comprises at least one of radiotherapy and chemotherapy. For instance, the anhydrous disordered crystalline compound may be advantageously used in combination with radiotherapy. An example of evidence for the therapeutic efficacy provided by (S)-[2-chloro-4-fluoro-5-(7-morpholin-4-yl-quinazolin-4-yl)phenyl]-(6-methoxy-pyridazin-3-yl)-methanol in combination with radiotherapy is set out in EXAMPLE 5. In other embodiments, the cancer treatment further comprises chemotherapy, i.e. administration of at least one other anticancer agent. For instance, the other anticancer agent may be selected from etoposide. In still further embodiments, the cancer treatment comprises both radiotherapy and chemotherapy, for instance administration of etoposide and radiotherapy.

Accordingly, the present invention provides a method of treating a patient in need thereof, comprising administering anhydrous disordered crystalline (S)-[2-chloro-4-fluoro-5-(7-morpholin-4-yl-quinazolin-4-yl)phenyl]-(6-methoxy-pyridazin-3-yl)-methanol, respectively a pharmaceutical composition comprising same according to the invention, to the patient. In analogy to what has been disclosed above, treating the patient may further comprise at least one of treatment by radiotherapy and chemotherapy.

Analytical Methods:

Powder X-Ray Diffraction Pattern (XRPD) was obtained by standard techniques as described in the European Pharmacopeia $7^{th}$ Edition chapter 2.9.33 (Cu—$K_{\alpha 1}$ radiation, $\lambda$=1.5406 Å, Stoe StadiP 611 KL transmission diffractometer, ambient temperature); and in particular:

The measurement was performed in transmission geometry with Cu—K, radiation on a Stoe StadiP 611 diffractometer equipped with Mythen1K Si-strip detector (PSD). Approximately 10-100 mg of the sample were prepared between amorphous films. The measurement was carried out by setting following parameters:

angular range: 1°-41°2θ
angular resolution: 0.015 °2θ
PSD step with: 0.49°2θ
measurement time: 15 s/PSD-step
generator settings: 40 mA, 40 kV

DSC:

DSC measurement was acquired on a Mettler-Toledo heat-flux Differential Scanning Calorimeter system DSC 1. Approximately 1-5 mg sample amount were weighed accurately in a 40 µl Aluminium pan with pierced lid. The scan was carried out from 25° C. to 350° C. with a linear heating rate of 5 K/min and a nitrogen purge gas at 50 mL/min.

TGA:

The sample was investigated on a Mettler-Toledo Thermogravimetric Analyser TGA 851 with autosampler, using a nitrogen inert gas atmosphere (flow 50 mL/min). Approximately 5-20 mg sample amount were weighed accurately in a 100 µl Aluminium pan and hermetically closed by an Aluminium lid. Just before insertion to the oven the lid was pierced by a needle of the autosampler system. The Scan was carried out from 25° C. to 350° C. at 5 K/min. The result was baseline-corrected with a blank run from an empty 100 µl Aluminium pan of the same type, using the identical temperature profile.

Solubility Measurements:

Test media:

SGF (Simulated gastric fluid without pepsin) pH 1.2:
2.0 g sodium chloride were placed in a 1 L volumetric flask and dissolved in around 500 mL water. 80 mL of 1 M hydrochloric acid solution were added and the volume made up to 1 L.

The resulting SGF solution contains: 34.2 mM sodium chloride

FaSSIF (Fasted State Simulated Intestinal Fluid) pH 6.5:
0.224 g SIF powder (obtained from biorelevant.com) were dissolved in FaSSIF buffer in a 100 mL volumetric flask and made up to volume. The FaSSIF medium was allowed to equilibrate for 2 h at ambient room temperature and used within 48 h of preparation. FaSSIF buffer can be made up by dissolving 0.42 g NaOH pellets, 3.44 g of monobasic sodium phosphate anhydrous and 6.19 g sodium chloride in about 0.9 L of purified water, adjusting the pH to 6.5 with 1 N NaOH or 1 N HCl and making up the volume to 1 L.

The resulting FaSSIF contains: 3 mM sodium taurocholate; 0.75 mM lecithin; 105.9 mM sodium chloride; 28.4 mM monobasic sodium phosphate and 8.7 mM sodium hydroxide.

FeSSIF (Fed State Simulated Intestinal Fluid) pH 5.0:
1.12 g SIF powder (biorelevant.com) were dissolved in FeSSIF buffer in a 100 mL volumetric flask and made up to volume. It was used within 48 h of preparation. FeSSIF buffer can be made up by dissolving 4.04 g NaOH pellets, 8.65 g of glacial acetic acid and 11.87 g sodium chloride in about 0.9 L of purified water, adjusting the pH to 6.5 with 1 N NaOH or 1 N HCl and making up the volume to 1 L.

The resulting FeSSIF contains: 15 mM sodium taurocholate; 3.75 mM lecithin; 203.2 mM sodium chloride; 101.0 mM sodium hydroxide and 144.1 mM acetic acid.

Solubility Measurements:

Excess amount of substance was weighed into Uniprep® Whatman vials, to which 1 mL of test medium were added. The suspension was shaken for 24 h at 450 rpm (rounds per minute) at 37° C. The pH was measured at 1 h, 6 h and 24 h and the vials were checked for undissolved compound. The pH of the medium was adjusted wherever necessary. After 24 h, the solutions were filtered through 0.2 µm PTFE membrane filter and the filtrates analysed using HPLC after suitable dilutions.

HPLC:

Apparatus: Agilent 1100
Column: Chromolith® Performance RP-18e100-3 mm, Art. 1.52001 (h)
Wavelength: 282 nm
Injection volume: 5 µL
Column Oven: 37° C.
Auto sampler: 37° C.
Eluent A for HPLC: Formic Acid:Ultrapure water (1:999;v/v)
Eluent B for HPLC: Formic Acid+Acetonitrile (1:999;v/v)
HPLC-Gradient:

| Time (minutes) | Eluent A (%) | Eluent B (%) | Flow (mL/min) |
| --- | --- | --- | --- |
| 0.00 | 90 | 10 | 1.70 |
| 0.30 | 90 | 10 | 1.70 |
| 2.00 | 10 | 90 | 1.70 |
| 2.75 | 10 | 90 | 1.70 |
| 2.76 | 90 | 10 | 2.50 |
| 4.00 | 90 | 10 | 2.50 |

The invention will now be described with regard to exemplary embodiments of the present invention, which shall not be regarded as limiting. As used herein, "substance", "API" or "compound" refer to (S)-[2-chloro-4-fluoro-5-(7-morpholin-4-yl-quinazolin-4-yl)phenyl]-(6-methoxy-pyridazin-3-yl)-methanol.

Example 1

49.6 g API were dissolved in 305 g dichloromethane/methanol, 9:1. 186 g n-heptane were filled into a 250 mL reactor. Within approx. 6 min 108 g of the API solution were added directly into the vortex of the stirred n-heptane. The solid-/liquid-separation was done by filtration and the solid material was dried.

Example 2

1.2 g API were nearly dissolved in 55 mL dichloromethane at room temperature and the slightly turbid solution was filtered through a 0.2 µm syringe filter. The obtained clear solution was added fast to 120 mL n-heptane at room temperature and an immediate precipitation was observed. The solid-/liquid-separation was done by filtration and the solid material was dried overnight at 50° C. with a dry Nitrogen flow.

Example 3

Approx. 20-30 mg API were nearly dissolved at room temperature in several solvents (see table below) and the slightly turbid solutions were filtered through 0.2 µm syringe filters. The obtained clear solutions were added fast to several anti-solvents (see table below) at room temperature and immediate precipitations were observed. The solid-/liquid-separations were done by centrifugation and the solid materials were dried overnight at room temperature with a dry nitrogen flow. The solvent-anti-solvent combinations are compiled in the table below.

| Amount API | Solvent | Volume [mL] | Anti-Solvent | Volume [mL] |
|---|---|---|---|---|
| 28 mg | Dichloromethane | 1 | n-Heptane | 2 |
| 19 mg | Methanol | 6 | Water | 12 |
| 27 mg | 1,4-Dioxane | 2 | Water | 8 |
| 19 mg | Tetrahydrofurane | 1.5 | n-Heptane | 3 |

Example 4

15.5 Liter of stirred DMSO were degassed by 3 cycles of a nitrogen flow followed by a vacuum evacuation, respectively. 1.7 kg API were added to the stirred DMSO solution at room temperature until a clear solution was obtained (after approx. 15 min stirring). The solution was filtered under vacuum through a filter cartridge (polish filtration). 172.3 Liter of water were filled into a clean reactor. Afterwards, the API solution in DMSO was added drop-wise within 30 min directly into the vortex of the stirred water. The resulting suspension was stirred at room temperature for 30 min, filtered and the filter-cake was washed with water. Then, the wet API was charged back to the reactor, filled up with 17.5 Liter water and stirred for 1 hour at room temperature. The API was isolated again by filtration. Three different wet sub-lots were combined by slurry in 60.7 Liter Water. The final solid-/liquid-separation was done by filtration and the solid material was dried under vacuum at 70° C. over night.

Example 5: Therapeutic Efficacy

The therapeutic relevance of DNA-PK inhibition by the drug substance as such was investigated in vivo in combination with ionizing radiation (IR), a clinically established DSB-inducing treatment. The drug substance was tested for activity in six xenograft mouse models of human cancer. The models were chosen from different cancer indications (colon, lung, head and neck, pancreatic), and histological subtypes (adeno, squamous, large cell). Ionizing radiation was administered using a fractionated schedule of 2 Gy per day administered over five consecutive days (total radiation dose=10 Gy). was given orally 10 min prior to each fraction of radiation (ONC397-1-2AZ, ONC397-1-3AZ, ONC397-1-4AZ, ONC397-1-5AZ, ONC397-1-8AZ).

In all models, oral administration of the drug substance resulted in a strong enhancement of the radiation effect. The radiotherapy enhancing effect was quantified across the tested models by the time to reaching 400% initial volume for the 150 mg/kg study arms. The resulting Kaplan-Meier plots were compared by the log-rank test. The enhancement ratio in this treatment setting was found to be between 1.5 (A549, HCT116), and 2.6 (NCI-H460).

The invention claimed is:

1. An anhydrous disordered crystalline (S)-[2-chloro-4-fluoro-5-(7-morpholin-4-yl-quinazolin-4-yl)-phenyl]-(6-methoxy-pyridazin-3-yl)-methanol.

2. The anhydrous disordered crystalline (S)-[2-chloro-4-fluoro-5-(7-morpholin-4-yl-quinazolin-4-yl)-phenyl]-(6-methoxy-pyridazin-3-yl)-methanol according to claim 1, which is characterized by a powder X-ray diffraction pattern having at least two peaks at degrees two theta selected from the group consisting of 3.9, 5.1, 6.1, 8.4, 10.7, 12.7, 14.6, and 22.8, each ±0.3 degrees two theta, wherein each of the at least two peaks is characterized by having a full width at half maximum of equal to or greater than 0.2 degrees two theta.

3. The anhydrous disordered crystalline (S)-[2-chloro-4-fluoro-5-(7-morpholin-4-yl-quinazolin-4-yl)-phenyl]-(6-methoxy-pyridazin-3-yl)-methanol according to claim 2, wherein the powder X-ray diffraction pattern has at least one further peak at degrees two theta selected from 3.1, 9.9, 13.5, 16.0, 16.5, 18.0, 19.0, 20.9, 21.9, 22.8, 24.0, 24.9, and 25.4 each ±0.2 degrees two theta.

4. The anhydrous disordered crystalline (S)-[2-chloro-4-fluoro-5-(7-morpholin-4-yl-quinazolin-4-yl)-phenyl]-(6-methoxy-pyridazin-3-yl)-methanol according to claim 1, which is characterized by a powder X-ray diffraction pattern substantially in accordance with FIG. 1 or 2.

5. The anhydrous disordered crystalline (S)-[2-chloro-4-fluoro-5-(7-morpholin-4-yl-quinazolin-4-yl)-phenyl]-(6-methoxy-pyridazin-3-yl)-methanol according to claim 1, which is characterized by a differential scanning calorimeter profile substantially in accordance with FIG. 3.

6. The anhydrous disordered crystalline (S)-[2-chloro-4-fluoro-5-(7-morpholin-4-yl-quinazolin-4-yl)-phenyl]-(6-methoxy-pyridazin-3-yl)-methanol according to claim 1, which has a solubility in a simulated gastric fluid without pepsin at a pH of 1.2 of at least about 1900 µg/ml.

7. The anhydrous disordered crystalline (S)-[2-chloro-4-fluoro-5-(7-morpholin-4-yl-quinazolin-4-yl)-phenyl]-(6-methoxy-pyridazin-3-yl)-methanol according to claim 1, which is obtainable by antisolvent precipitation.

8. A process for preparing anhydrous disordered crystalline (S)-[2-chloro-4-fluoro-5-(7-morpholin-4-yl-quinazolin-4-yl)-phenyl]-(6-methoxy-pyridazin-3-yl)-methanol, comprising:
    antisolvent precipitating of (S)-[2-chloro-4-fluoro-5-(7-morpholin-4-yl-quinazolin-4-yl)-phenyl]-(6-methoxy-pyridazin-3-yl)-methanol.

9. The process according to claim 8, wherein the antisolvent precipitating comprises:
    a) preparing a clear solution of (S)-[2-chloro-4-fluoro-5-(7-morpholin-4-yl-quinazolin-4-yl)-phenyl]-(6-methoxy-pyridazin-3-yl)-methanol in a solvent or solvent mixture, optionally with heating,
    b) combining the clear solution with an antisolvent to generate a suspension of (S)-[2-chloro-4-fluoro-5-(7- morpholin-4-yl-quinazolin-4-yl)-phenyl]-(6-methoxy-pyridazin-3-yl)-methanol in a solvent/antisolvent mixture, c) separating the obtained anhydrous disordered crystalline (S)-[2-chloro-4-fluoro-5-(7-morpholin-4-yl-quinazolin-4-yl)-phenyl]-(6-methox-pyridazin-3-yl)-methanol from the solvent/antisolvent mixture, and d) drying the anhydrous disordered crystalline (S)-[2-chloro-4-fluoro-5-(7-morpholin-4-yl-quinazolin-4-yl)-phenyl]-(6-methoxy-pyridazin-3-yl)-methanol.

10. The process according to claim 9, wherein the solvent or solvent mixture is selected from the group consisting of dimethyl sulfoxide, dichloromethane, methanol, 1,4-dioxane, tetrahydrofuran, and mixtures thereof.

11. The process according to claim 9, wherein the antisolvent is at least one selected from the group consisting of acetone, n-heptane and water.

12. The process according to claim 9, wherein the solvent is at least one selected from the group consisting of dichloromethane, methanol and 1,4-dioxane, and the antisolvent is water; or the solvent is tetrahydrofuran and the antisolvent is n-heptane.

13. A pharmaceutical composition, comprising:
the anhydrous disordered crystalline (S)-[2-chloro-4-fluoro-5-(7-morpholin-4-yl-quinazolin-4-yl)-phenyl]-(6-methoxy-pyridazin-3-yl)-methanol according to claim 1, and
optionally at least one excipient.

14. A method for inhibiting DNA-dependent protein kinase in a cancer that expresses DNA-PK, comprising:
administering the anhydrous disordered crystalline (S)-[2-chloro-4-fluoro-5-(7-morpholin-4-yl-quinazolin-4-yl)-phenyl]-(6-methoxy-pyridazin-3-yl)-methanol to a patient in need thereof, optionally in combination with at least one selected from the group consisting of chemotherapy and radiotherapy.

15. A pharmaceutical composition, comprising:
the anhydrous disordered crystalline (S)-[2-chloro-4-fluoro-5-(7-morpholin-4-yl-quinazolin-4-yl)-phenyl]-(6-methoxy-pyridazin-3-yl)-methanol according to claim 1, and
at least one excipient.

16. The pharmaceutical composition according to claim 15, wherein the at least one excipient is selected from the group consisting of a filler, a binder, a humectant, a disintegrating agent, a wicking agent, a matrix former and a lubricant.

* * * * *